Figure 1:
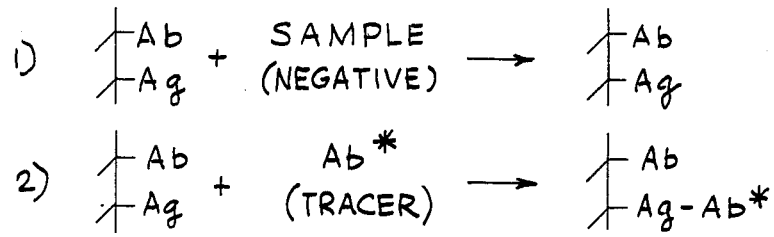
Figure 1:
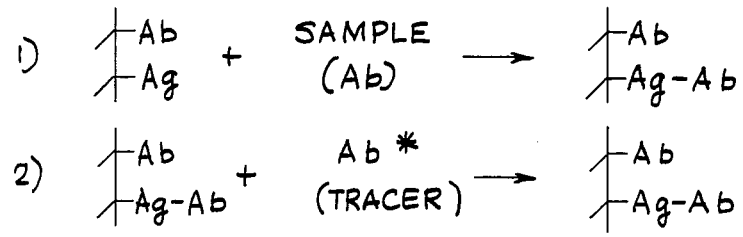
Figure 1:
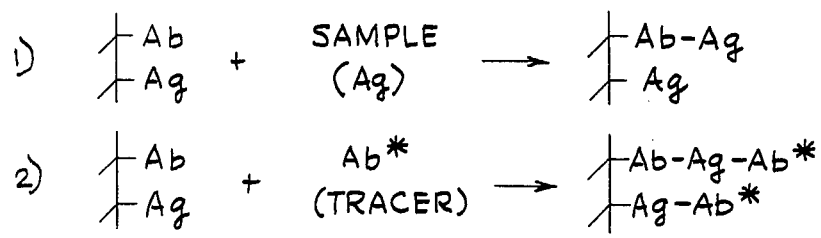
Figure 2:
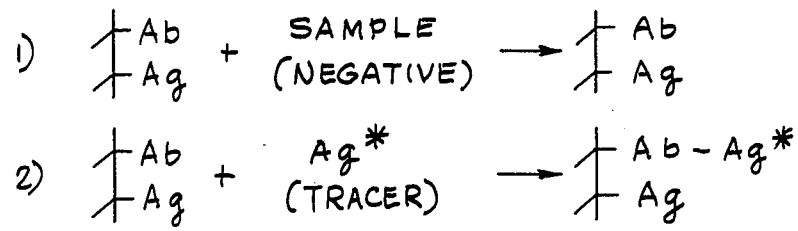
Figure 2:
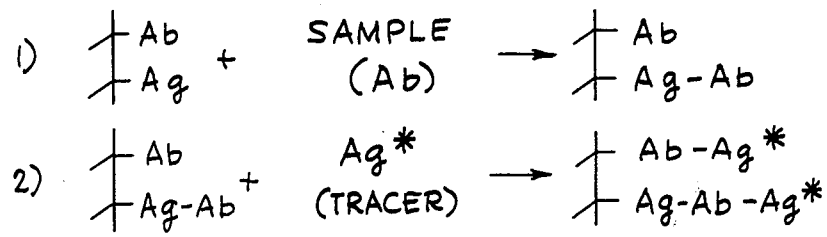
Figure 2:
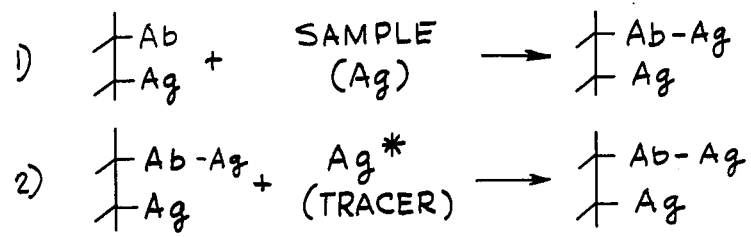

United States Patent [19]

O'Neill

[11] 4,242,322

[45] Dec. 30, 1980

[54] METHODS AND MATERIALS FOR DETECTING ANTIGENS AND ANTIBODIES

[75] Inventor: Sean P. O'Neill, Bethesda, Md.

[73] Assignee: Electro-Nucleonics Laboratories, Inc., Bethesda, Md.

[21] Appl. No.: 913,508

[22] Filed: Jun. 7, 1978

[51] Int. Cl.² .................... G01N 33/16; A61K 43/00; A61K 39/00
[52] U.S. Cl. ..................................... 424/1; 23/230 B; 424/12; 424/7
[58] Field of Search ................ 424/1, 12, 7; 23/230 B

[56] References Cited

U.S. PATENT DOCUMENTS

| Re. 29,955 | 4/1979 | Bornstein et al. | 424/1 |
| 3,949,064 | 4/1976 | Bornstein et al. | 424/1 |

Primary Examiner—Benjamin R. Padgett
Assistant Examiner—Christine M. Nucker

[57] ABSTRACT

Bifunctional immunoadsorbents containing complementary antigens and antibodies which are useful for detecting the presence of complementary antigens and antibodies in serum are described.

15 Claims, 2 Drawing Figures

A    BIA WITH NEGATIVE SAMPLE

RESULT: CONTROL LEVEL OF TRACER MOLECULES ON BIA

B    BIA WITH EXCESS ANTIBODY CONTAINING SAMPLE

RESULT: DECREASE IN TRACER MOLECULES ON BIA

C    BIA WITH EXCESS ANTIGEN CONTAINING SAMPLE

RESULT: INCREASE IN TRACER MOLECULES ON BIA

A    BIA WITH NEGATIVE SAMPLE

RESULT: CONTROL LEVEL OF TRACER MOLOCULES ON BIA

B    BIA WITH EXCESS ANTIBODY CONTAINING SAMPLE

RESULT: INCREASE IN TRACER MOLOCULES ON BIA

C    BIA WITH EXCESS ANTIGEN CONTAINING SAMPLE

RESULT: DECREASE IN TRACER MOLOCULES ON BIA

METHODS AND MATERIALS FOR DETECTING ANTIGENS AND ANTIBODIES

BACKGROUND OF THE INVENTION

Investigations of antigen-antibody systems frequently require sensitive methods for the detection of each component. The course of an infectious disease, for example, can be followed by determinations of the presence or absence of antigens or antibodies in serum, and their relative amounts. At the outset of the disease, the antigen will be in excess. As the body marshals its defenses, the relative amount of antibody present increases. When the infection subsides, the ratio of antibody to antigen increases until, finally, there is no detectable antigen.

Sensitive detection of antigenic substances is conveniently carried out by a solid phase competitive radioimmunoassay (RIA). This procedure cannot be used, however, if the test sample contains antibody since this will interfere with the radioimmunoassay.

A solid-phase procedure which makes possible the accurate determination of either antigen or antibody particles in the presence of the other would be a significant advance in the art.

THE INVENTION

A procedure has now been discovered which makes possible the convenient detection of antigen or antibody when either of these products is present alone in a test sample. More importantly, it makes possible the independent determination of excess antibody or antigen, even though appreciable amounts of the minor component may be present in the test sample.

A particular advantage of the invention is that it avoids the necessity of having available purified antigen for labeling.

The process of the invention is adaptable to all of the conventional labeling techniques, including isotopes, enzymes and fluorescent materials. It is also adaptable to the various methods employed to detect a labeled reaction.

The crux of the invention is the provision of a bifunctional immunoadsorbent (BIA) containing bound antibody which is complementary to the antigen particle to be detected at a first site, and at a second site, bound antigen which is complementary to the antibody particle to be detected. BIA is capable of reacting with both antigens and antibodies in a test sample. The reaction product or conjugate thus formed may be conjugated to a labeled antigen or antibody to form a second conjugate. The amount of second conjugate which is formed, as determined by measuring the amount of labeled material present, is a measure of the amount of antigen or antibody present in the test sample.

The processes and products of the invention will be best understood by reference to the figures.

FIG. I illustrates the use of a labeled antibody.

FIG. II illustrates the use of a labeled antigen.

FIG. IA represents the situation when BIA is exposed first to a negative sample containing neither antigen nor antibody, and then to a labeled antibody. The BIA does not react with the sample since there is no complement. When the BIA is then contacted with the labeled antibody, there is a complement reaction, with a net increase in tracer level of the final product.

FIG. IB illustrates the reactions when the sample contains excess antibody. Initially, the free antigen on the BIA conjugates with the antibody in the sample. As a result, there is no possibility of a complement reaction with the antibody. It follows, as shown, that there is a decrease in tracer level of the final product compared with the final product from the negative sample.

FIG. IB shows, by similar analysis, that when the sample contains antigen, there is a net increase in tracer level of the final product compared to the negative sample.

FIG. IC shows the reactions when the sample contains excess antigen.

FIG. IIA, B and C are analogous to FIG. IA, B and C, except that a labeled antigen is employed. Again, the negative control provides the base. However, with an antigen label, there is an increase in tracer level of the final product when the sample contains excess antibody, and a decrease in tracer level of the final product when the sample contains excess antigen. This is in contrast to the situation represented by FIG. IA, B and C.

The above is summarized in Table I.

TABLE I

| | Tracer Level* | |
|---|---|---|
| | Excess Antibody | Excess Antigen |
| Antibody label | Decreases | Increases |
| Antigen label | Increases | Decreases |

*Compared to negative contrast

There are, of course, appropriate washes between each step to remove the sample and excess labeled tracer. These are illustrated in the examples.

The method of the invention, as will be apparent from the above, is a method for detecting the presence of antigen or antibody in serum which comprises the steps of:

(1) incubating the serum to be tested with a bifunctional immunoadsorbent containing bound, complementary antigen and antibody, whereby antigen and antibody present in the serum conjugates with its complement on the immunoadsorbent, (2) incubating resulting product with labeled antigen or antibody, (3) determining the extent to which the labeled antigen or antibody becomes bound to the said product.

It will be apparent from a consideration of the figures why it is that only the excess particle, whether antigen or antibody, is measured. It will be apparent also why the particle which is present in the lesser amount does not interfere. Consider, for example, IB which illustrates the end result when the sample contains excess antibody. It will be apparent that any antigen in the sample will conjugate with antibody on the BIA. However, since excess antibody is present, the conjugated antibody will be neutralized by reaction with antibody. FIG. IB then, illustrates a simplified version of the reaction sequence, since the final product is shown as containing only two antibodies and one antigen. In fact, the final product could have lengthy chains of alternating antibodies and antigen, but each chain would be terminated by an antibody. The balance of the figures can be similarly analyzed with the same results.

The BIA of this invention can take any of a number of forms. The preferred form is one in which the antigens and antibodies are adsorbed on the surface of particles such as glass, plastic or charcoal which may be porous or nonporous. The particles can be used alone, or they can be pressed into pills using conventional inert binders such as glucose. Alternatively, the BIA can be the inside of the test tube with the particles adsorbed on the inner surface.

The BIA can be prepared using a variety of different procedures. One very convenient procedure is to saturate the substrate, e.g. porous glass beads with antigen and to then expose the saturated substrate to a concentration of antigens which is less than saturation, say for example, one half saturation. The result will be that the antigen will all bind with the antibody, but since there is less antigen than antibody, the BIA will have both antibody and antigen sites. The BIA can also be a mixture of particles with antigen adsorbed on one portion and antibody on another. This aspect of the invention is specifically included within the scope of the term BIA. The adsorbed particles may be cross linked with a bifunctional compound such as gluteraldehyde to increase the tenacity with which the particles cling to the surface.

As indicated above, isotope, fluorescent and enzyme labels can be employed in the practice of this invention. Typically useful isotopes include $^{14}C$, $^{131}I$, $^{125}I$, $^{3}H$ and $^{35}S$. Enzymes which may be employed include, for example, peroxidase, $\beta$-glucuronidase, $\beta$-D-glucosidase, $\beta$-D-galactosidase, urease, glucose oxidase plus peroxidase, galactose oxidase plus peroxidase and acid or alkaline phosphotase. Fluorescein, rhodamine and auramine are typically useful fluorescent materials.

These materials are employed in the usual manner. They are used to label selected antigens or antibodies by conventional methods. For example, the enzymes are conjugated to the selected substrate with bridging molecules, such as carbodiimide, diisocyanate or gluteraldehyde.

The measuring techniques are the same as normally employed in immunological measurements. Isotopes are measured with any of the commercially available counting tools. Fluorescent materials are measured in a fluorimeter. Enzyme conjugates are incubated with selected substrates, the reaction stopped with, for example, enzyme inhibitors, and the extent of color development determined by any of the usual techniques.

Since the formation of the tracer antigens and antibodies and the measuring method selected to determine their presence are conventional, they are not discussed in detail.

A particular advantage of this invention is that it avoids the problem of isolating pure viruses and separating antigen from them. This is a serious problem in clinical tests for many infections. In the usual procedure, a pure virus is cultivated and used as a source of antigen. This antigen is isolated from the virus in as pure a form as possible, and used to immunize a suitable animal such as a rabbit, goat or horse to stimulate the production of antibody. The antibody, in turn, is used to test for the presence of antigen in a subject suspected of infection by the virus.

In the system of this invention, neither purified antigen or antibody are needed to form the BIA. Purified antibody for the preparation of tracers are readily isolated from the sera of infected humans, or from the sera of immunized animals.

The methods and products of this invention have been described without reference to specific antigens or antibody for the reason that it is not so limited. In fact, so far as is known, it is theoretically applicable to all antigens and antibodies. They can be used, for example, with infections such as hepatitis, gonorrhea, syphilis, pneumonia, tuberculosis and other infections characterized by antigen-antibody reactions.

The products of this invention can be made available for clinical use in a number of suitable kits which will include the various reagents and chemicals applicable to the selected labeling technique. A typical kit for use in an isotopic tracer procedure will contain the BIA, the labeled tracer, and a buffer solution for washing. It may also contain negative controls, but large clinical laboratories may set up their own controls. The BIA may be simply a treated test tube as described above, a quantity of loose particles, or a pressed pill. The labeled tracer may be an antigen or antibody labeled with a measureable amount of isotope. The buffer will normally be phosphate buffered saline. The control may be a serum sample known to be free of the antigen and antibody under test.

A kit for enzyme testing would be similar, except that the label on the tracer would be an enzyme. Additionally, it would contain a substrate for the enzyme and a reagent to terminate the enzyme reaction.

A kit for fluorescent testing would contain a fluorescent labeled antibody or antigen.

The following non-limiting examples are given by way of illustration only.

EXAMPLE 1

Preparation of BIA 1. 1 gm of controlled-pore glass particles was shaken with 10 ml of goat antisera to hepatitis surface antibody (HBsAg) and 10 ml of phosphate buffered saline (PBS, 0.1 M, pH 6.0) for 1 hour at room temperature.

2. The glass particles were allowed to settle and the liquid above the glass decanted.

3. The glass was rinsed with 30 ml of tap water to remove the remaining liquid from step 1.

4. 20 ml of a solution of 0.25% gluteraldehyde in phosphate buffer (0.1 M, pH 6.0) was added to the glass particles.

5. The slurry of glass-liquid was shaken for 3 hours at room temperature.

6. The glass was allowed to settle and the liquid decanted.

7. The glass particles were rinsed with 30 ml of PBS for each rinse.

8. 20 ml of a human serum sample containing a known, low level of hepatitis surface antigen (HBsAg) was added to the glass particles.

9. The mixture of glass and human serum was shaken for 1 hour at room temperature.

10. The serum was decanted from the settled glass particles.

11. The glass was washed 5 times with 30 ml volumes of PBS per wash.

12. The glass particles were tested for uptake of radioactively-labelled $^{125}I$-antibody to establish that both antibody and antigen had been absorbed.

13. The BIA was stored as a wet slurry in water at 2°–8° C.

The controlled pore glass particles used in this example were obtained from Electro-Nucleonics, Inc. They are 200–400 mesh in particle size with pore diameters ranging from 2000 to 3000 angstroms.

EXAMPLE 2

Preparation of Pills

One gram of BIA prepared as in Example 1 was mixed with the following components:
Polyvinyl alcohol: 0.2 gm
Sucrose: 1.0 gm
Primagel: 0.05 gm
Carbowax: 0.02 gm
The mixture was dried and passed through a pilling machine to produce pills, each weighing 7 mg and containing 3 mg of BIA.

EXAMPLE 3

Radioimmunoassay for HBsAg and Anti-HBs Antibody 1. 0.2 ml of a test sample was added to an assay tube containing 1 pill of BIA (7 mg) and 1 small magnet. Ten negative controls were run with each assay.
2. The mixtures were mechanically agitated for 4 hours at room temperature.
3. Each tube was aspirated down to within 2–3 mm of the settled glass surface.
4. 1 ml of buffer (PBS) was added to each tube.
5. After magnetic agitation for 1 minute, the glass settled for 1½ minutes and the supernatant aspirated and discarded.
6. 0.1 ml of radioactively-labeled anti-HBs antibody (100,000 dpm of radioactivity) was added to each tube.
7. The mixtures were agitated magnetically for 1 hour at room temperature.
8. The liquid solution above the settled glass was aspirated as in step 3. The aspirate was discarded.
9. The glass particles were washed 4 times following the procedure of steps 5 and 6.
10. Each assay tube was counted in a gamma counter to determine the quantity of radioactive $^{125}$I-antibody bound to the BIA.
11. Results were interpreted as:
 1. Test samples were considered positive for HBsAg when bound radioactive counts were 30% or more above the count for the mean of the 10 negative controls.
 2. Test samples were considered positive for anti-HBs antibody when bound radioactive counts were 30% below the negative control mean.
 3. Test samples with counts within ±30% of the negative control were considered negative for HBsAg and anti-HBs antibody.

EXAMPLE 4

Enzyme Immunoassay for HBsAg and Anti-HBsAg Antibody

1–5. Steps 1–5 were identical to the RIA procedure of Example 3, except the tubes were shaken, not magnetically mixed. No magnet is included.
6. 0.05 ml of horseradish peroxidase coupled to anti-HBs antibody (HRPO-Ab) were added to each assay tube.
7–9. Steps 7–9 are identical to the RIA, except the tubes were shaken not magnetically mixed.
10. 0.5 ml of substrate solution was added to each tube. The substrate solution used was made as follows:
 1. 97 mg of 4-amino-antipyrene was dissolved in 500 ml of phosphate buffer (0.05 M pH 7.0).
 2. 0.6 gm of phenol was also dissolved in another 500 ml of the same buffer.
 3. Solutions (1) and (2) were combined in equal volumes.
 4. 0.001 ml of 3% hydrogen peroxide was added to each 1 ml of solution (3).
11. The BIA and substrate solution were shaken at room temperature for 2 hours.
12. The glass was allowed to settle and a 0.4 ml volume of solution was removed from each assay tube and transferred to a spectrophotometer cuvette.
13. The optical density (O.D.) of each solution at 510 millimicrons was read.
14. O.D. readings for the 10 negative controls were averaged to give a mean negative control.
15. Test samples with O.D. values 30% greater than the negative mean were considered positive for HBsAg; test samples with O.D. values 30% less than the negative mean were considered positive for anti-HBs antibody.

What is claimed is:

1. A method for detecting the presence of antigen or antibody particles in serum which comprises
 1. incubating the serum containing the antigen or antibody particles to be detected with a bifunctional immuno-adsorbent characterized by the presence of a first site containing bound antibody which is complementary to the antigen particle to be detected, and a second site containing bound antigen which is complementary to the antibody particle to be detected, whereby the antigen or antibody particles present in the serum conjugates with its complementary antibody or antigen on the immunoadsorbent,
 2. incubating the resulting product with labeled antigen or antibody, and
 3. determining the extent to which the labeled antigen or antibody becomes bound to the said product.
2. A method as in claim 1 wherein a labeled antibody is used in Step 2.
3. A method as in claim 2 wherein the antibody label is an isotope.
4. A method as in claim 2 wherein the antibody label is an enzyme.
5. A method as in claim 2 wherein the antibody label is a fluorescent material.
6. A method as in claim 1 wherein a labeled antigen is used in Step 2.
7. A method as in claim 6 wherein the antigen label is an isotope.
8. A method as in claim 6 wherein the antigen label is an enzyme.
9. A method as in claim 6 wherein the antigen label is a fluorescent material.
10. A bifunctional immunoadsorbent containing complementary antibody at a first site and antigen at a second site.
11. A bifunctional immunoadsorbent containing complementary antibody at a first site and antigen at a second site on glass particles.
12. An immunoadsorbent of claim 11 wherein the glass particles are porous.
13. A bifunctional immunoadsorbent which is a test tube having on its inner surface complementary adsorbed antibody at a first site and adsorbed antigen at a second site.
14. A bifunctional immunoadsorbent of claim 10 comprising a mixture of adsorbeng particles with adsorbed antigen on one fraction thereof and complementary adsorbed antibody on another fraction.
15. A bifunctional immunoadsorbent of claim 11 in which the glass particles are pressed into a pill form containing binder adjuvants.

* * * * *